United States Patent
Schwendeman et al.

(10) Patent No.: US 8,017,718 B2
(45) Date of Patent: Sep. 13, 2011

(54) VINYL ETHERS AND COMPOSITIONS CONTAINING THEM

(75) Inventors: John E. Schwendeman, Wexford, PA (US); M. Lisa Perrine, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 299 days.

(21) Appl. No.: 12/129,794

(22) Filed: May 30, 2008

(65) Prior Publication Data

US 2008/0227927 A1 Sep. 18, 2008

Related U.S. Application Data

(62) Division of application No. 11/424,621, filed on Jun. 16, 2006, now Pat. No. 7,411,033.

(51) Int. Cl.
*C08G 63/06* (2006.01)

(52) U.S. Cl. ........ 528/361; 525/408; 528/271; 528/272; 528/274; 526/319; 522/115

(58) Field of Classification Search ................. 525/408; 528/361, 271, 272, 274; 526/319; 522/115
See application file for complete search history.

(56) References Cited

U.S. PATENT DOCUMENTS

| | | | |
|---|---|---|---|
| 2002/0076504 A1* | 6/2002 | Klinkenberg et al. | 427/508 |
| 2003/0134926 A1* | 7/2003 | Fukada et al. | 522/81 |
| 2004/0072979 A1* | 4/2004 | Sheridan et al. | 526/319 |
| 2006/0128825 A1* | 6/2006 | Fansler et al. | 522/115 |

* cited by examiner

*Primary Examiner* — James Seidleck
*Assistant Examiner* — Gregory Listvoyb
(74) *Attorney, Agent, or Firm* — Donald R. Palladino

(57) ABSTRACT

Disclosed are vinyl ethers and related compositions. The vinyl ethers are the conjugate addition reaction product of reactants comprising a vinyl ether group-containing acrylic ester and a nucleophile.

16 Claims, No Drawings

VINYL ETHERS AND COMPOSITIONS CONTAINING THEM

CROSS-REFERENCE TO RELATED APPLICATION

This application is a division of U.S. patent application Ser. No. 11/424,621, filed Jun. 16, 2006, now U.S. Pat. No. 7,411,033, the contents of which are incorporated by reference herein.

FIELD OF THE INVENTION

The present invention relates to vinyl ethers and related compositions. More particularly, the present invention is directed to vinyl ethers that are the conjugate addition reaction product of a reaction of a vinyl ether group-containing acrylic ester with a nucleophile.

BACKGROUND OF THE INVENTION

Radiation curable compositions, such as coating and adhesive compositions, are used in a wide variety of applications. These compositions are cured by a photocuring process that involves the radiation induced polymerization or cross linking of polymerizable materials into a three dimensional network. Often it is desirable to use radiation curable compositions because they can require little or no volatile solvents, which is, of course, beneficial because of the demands to eliminate volatile organic compounds from coatings and adhesives. Energy savings, high throughput rates (low cure times), and low energy requirements are also often strong driving forces behind the use of radiation curable compositions. Radiation curable compositions can be applied to virtually any type of substrate, such as plastic, glass, textile, fabrics, leather, metal, paper, and wood, among others.

Radiation curable compositions are often based on unsaturated polyesters, styrene and/or acrylate compounds, wherein polymerization is initiated by a free radical mechanism that is oxygen inhibited unless effected in an inert atmosphere, such as under a blanket of nitrogen. Although formulation with certain photoinitiators, such as those that undergo a bimolecular reaction with a hydrogen donor can reduce the inhibitory effect of air, this benefit is often realized at the expense of a reduced cure rate. Moreover, styrene and certain acrylates are known as sensitizers and skin irritants as well as being carcinogenic, so that specialized safety precautions must be taken to protect personnel from exposure.

Vinyl ether containing compounds (monomers, oligomers and polymers) are sometimes utilized in radiation curable compositions. These compounds can cure by both cationic and free radical mechanisms and generally do not exhibit the extent of the toxicity issues previously described with respect to styrene and acrylates.

In many cases, it is desirable to spray apply radiation curable compositions. One drawback, however, to the use of certain relatively inexpensive multifunctional vinyl ethers, such as triethylene glycol divinyl ether, in a spray application is that these materials are of relatively low molecular weight and, accordingly, often too volatile for practical use in a spray application. Multifunctional vinyl ethers of reduced volatility, on the other hand, are often significantly more expensive than their low molecular weight counterparts.

As a result, novel vinyl ethers that can be relatively inexpensive to produce and which can exhibit reduced volatility, such that they are suitable for use in, for example, radiation curable compositions, such as coating and adhesive compositions, are desired.

SUMMARY OF THE INVENTION

In certain respects, the present invention is directed to vinyl ethers formed from reactants comprising: (a) a vinyl ether group-containing acrylic ester represented by the general formula (I):

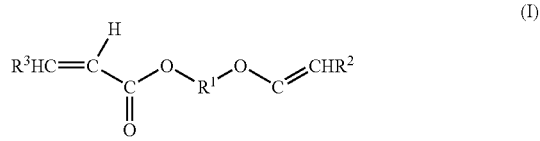

wherein $R^1$ represents an organic residue, and $R^2$ and $R^3$ each represent a hydrogen atom or an organic residue and may be the same or different; and (b) a nucleophile. Such vinyl ethers are made by a conjugate addition reaction of the nucleophile with the acrylate group of the vinyl ether group-containing acrylic ester.

In other respects, the present invention is directed to multifunctional vinyl ethers comprising a unit represented by the general formula (II):

wherein each VE represents the residue of a vinyl-ether group containing acrylic ester represented by the general formula (I) and may be the same or different and NU represents the residue of a nucleophile.

In still other respects, the present invention is directed to multifunctional vinyl ethers formed from reactants comprising: (a) a vinyl ether group-containing acrylic ester represented by the general formula (I); (b) a nucleophile comprising an enolate anion formed from an acetoacetate comprising an ester group or a malonic ester; and (c) a compound having a group reactive with the ester group of the acetoacetate or malonic ester. Such multifunctional vinyl ethers are made by a conjugate addition reaction of the enolate anion with the acrylate group of the vinyl ether group-containing acrylic ester.

In yet other respects, the present invention is directed to multifunctional vinyl ethers comprising a unit represented by the general formula (III):

wherein each VE represents the residue of a multi-functional vinyl ether comprising a unit represented by the general formula (I) and may be the same or different, each NU represents the residue of a nucleophile comprising an enolate anion formed from an acetoacetate or a malonic ester and may be the same or different, R represents the residue of a polyol, and n is an integer having a value of at least 1, such as 1 to 100.

The present invention is also directed to compositions, such as radiation-curable compositions, comprising such vinyl ethers, substrates at least partially coated with such compositions, as well as related methods.

DETAILED DESCRIPTION OF EMBODIMENTS OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

As indicated, certain embodiments of the present invention are directed to vinyl ethers. As used herein, the term "vinyl ether" refers to a compound, i.e., a monomer, oligomer, or polymer, that includes a vinyl ether group, which is a group represented by the structure —O—CH=CHR, wherein R is hydrogen or an organic residue. Certain embodiments of the present invention are directed to multifunctional vinyl ethers. As used herein, the term "multifunctional vinyl ether" refers to a compound, i.e., a monomer, oligomer, or polymer, having more than 1, such as 2 or more, vinyl ether groups per molecule.

In certain embodiments, the vinyl ethers of the present invention are formed from reactants comprising: (a) a vinyl ether group-containing acrylic ester represented by the general formula (I), described above, wherein $R^1$ represents an organic residue, and $R^2$ and $R^3$ each represent a hydrogen atom or an organic residue and may be the same or different; and (b) a nucleophile.

As used herein, the term "organic residue" refers to an organic group bound to a fundamental structure. For example, the organic residue represented by $R^1$ in the above general formula (I) may be, for example, straight, branched or cyclic alkylene groups containing 2 to 20 carbon atoms, alkylene groups containing 2 to 20 carbon atoms and having at least one oxygen atom in the form of an ether linkage and/or an ester linkage within the structure thereof, or aromatic groups which contain 6 to 11 carbon atoms and may optionally be substituted. Among them, alkylene groups having 2 to 6 carbon atoms and alkylene groups having 4 to 10 carbon atoms and having at least one oxygen atom in the form of an ether linkage are often desirable.

The organic residues represented by $R^2$ and $R^3$ in the above general formula (I) may be, for example, straight, branched or cyclic alkyl groups containing 1 to 10 carbon atoms or aromatic groups which contain 6 to 11 carbon atoms and may optionally be substituted. Among them, alkyl groups containing 1 to 2 carbon atoms and aromatic groups containing 6 to 8 carbon atoms are often desirable.

Non-limiting examples of vinyl ether group-containing acrylic esters suitable for use in the present invention are 2-vinyloxyethyl acrylate, 3-vinyloxypropyl acrylate, 1-methyl-2-vinyloxyethyl acrylate, 2-vinyloxypropyl acrylate, 4-vinyloxybutyl acrylate, 4-vinyloxycyclohexyl acrylate, 6-vinyloxyhexyl acrylate, 4-vinyloxymethylcyclohexylmethyl acrylate, 2-(vinyloxyethoxy)ethyl acrylate and 2-(vinyloxyethoxyethoxy)ethyl acrylate, including mixtures thereof.

The vinyl-ether group-containing acrylic esters suitable for use in the present invention can be made by any suitable technique. For example, such components can be produced according to any of the methods described in United States Patent Application Publication No. 2002/0143120 A1 at [0027] to [0034] and [0060] to [0128], the cited portions of which being incorporated herein by reference.

As previously indicated, the vinyl ethers of the present invention are formed from a nucleophile. As used herein, the term "nucleophile" refers to a reactant that participates in a chemical reaction by donating electrons, i.e., nucleophiles are electron donor compounds. As such, nucleophiles typically comprise anions such as, for example, fluorides (F—), cyanides (CN—), iodides (I—), chlorides (Cl—), bromides (Br—), acetates ($CH_3CO_2$—), enolates ($RCO_2C$—, wherein R is an organic residue), primary amines ($NH_2$—), secondary amines (—NHR, wherein R is an organic residue), ammonia (—$NH_3$), alkoxides (RO—, wherein R is an organic residue), hydrogen sulfides (HS—), alkyl sulfides, i.e., mercaptans (RS—, wherein R is an organic residue), hydroxides (OH—), and azides ($N_3$—), among others.

In certain embodiments, the nucleophile utilized to form a multifunctional vinyl ether of the present invention comprises an enolate anion formed from (i) a β-keto ester, which is a compound represented by the general structure

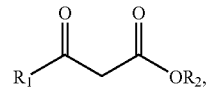

wherein $R_1$ and $R_2$ are each an organic residue and may be the same or different, such as an acetoacetate, wherein $R_1$ is a methyl group in the foregoing general structure, or (ii) a malonic ester, which is a compound represented by the general structure

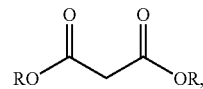

wherein each R is an organic residue and may be the same or different.

Acetoacetates suitable for use in the present invention include materials having an acetoacetate functionality of two, such as methyl acetoacetate, ethyl acetoacetate, t-butyl acetoacetate, 2-ethylhexyl acetoacetate, lauryl acetoacetate, acetoacetanilide, 2-acetoacetoxyethyl methacrylate, allyl acetoacetate; materials having an acetoacetate functionality of four, such as butanediol diacetoacetate, 1,6-hexanediol diacetoacetate, neopentyl glycol diacetoacetate, cyclohexanedimethanol diacetoacetate, ethoxylated bisphenol A diacetoacetate; materials having an acetoacetate functionality of six, such as trimethylolpropane triacetoacetate, glycerin triacetoacetate, polycaprolactone triacetoacetate; and materials having an acetoacetate functionality of eight, such as pentaerythritol tetraacetoacetate. Such materials are described in U.S. Pat. No. 5,945,489 at col. 2, line 46 to col. 9, line 10, the cited portion of which being incorporated herein by reference. Malonic esters suitable for use in the present invention include, for example, dimethyl malonate and diethyl malonate.

In certain embodiments, the reaction between the nucleophile and the vinyl-ether group-containing acrylic ester is conducted in the presence of a catalyst, such as potassium carbonate or any non-nucleophilic base, such as a hindered amine base catalyst. The amount of catalyst used can be whatever amount is desired to catalyze the reaction between the nucleophile and the vinyl-ether group-containing acrylic ester. In certain embodiments, the catalyst is present in an amount of up to 5 weight percent, such as 0.1 to 2 weight percent, based on the total weight of the nucleophile and the vinyl-ether group-containing acrylic ester.

The vinyl ethers of the present invention are the result of a conjugate addition reaction of the nucleophile with the acrylate group of the vinyl ether group-containing acrylic ester. As will be appreciated by those skilled in the art, compounds that have two double bonds separated by just one single bond are said to have "conjugated double bonds". When one of these double bonds is a C=O bond and the other a C=C bond, the compound, of the form C=C=O, can be attacked by nucleophiles at the carbonyl carbon and the beta (β) carbon, which is the carbon atom adjacent to the alpha (α) carbon. In a conjugate addition reaction, also referred to as a 1,4 addition, the addition takes place at the C=C bond rather than at the C=O bond. The Examples herein illustrate suitable methods and conditions for conducting such a reaction and producing a vinyl ether of the present invention.

As will be appreciated from the foregoing description, certain embodiments of the present invention are directed to multifunctional vinyl ethers comprising a unit represented by the general formula (II), described above, wherein each VE represents the residue of a vinyl-ether group containing acrylic ester represented by the general formula (I) and may be the same or different and NU represents the residue of a nucleophile comprising an enolate anion formed from an acetoacetate or a malonic ester, as described above. As a result, in certain embodiments, the present invention is directed to a multifunctional vinyl ether comprising a unit represented by the general formula (II), described above, wherein NU represents the residue of a compound represented by the general formula

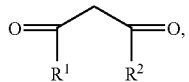

wherein $R^1$ and $R^2$ are organic residues and may be the same or different. In certain embodiments, $R^1$ is $CH_3$ or $OCH_2CH_3$ and/or $R^2$ is $OC(CH_3)_3$ or $OCH_2CH_3$.

In certain embodiments, such as in certain cases where a material having an acetoacetate functionality of two is used, and a multifunctional vinyl ether having a functionality greater than two is desired, a multifunctional vinyl ether of the present invention is formed by first reacting a malonic ester or an acetoacetate comprising an ester group with a compound having a group reactive with the ester group of the acetoacetate or malonic ester, such as an amine or, in some cases, a hydroxy functional compound, including, for example, a monofunctional alcohol and/or a polyol, and then reacting the resultant product with a vinyl ether group-containing acrylic ester represented by the general formula (I), described above, wherein $R^1$ represents an organic residue, and $R^2$ and $R^3$ each represent a hydrogen atom or an organic residue and may be the same or different. Suitable polyols include either low or high molecular weight materials and in general will have average hydroxyl values as determined by ASTM designation E-222-67, Method B, between 2000 and 10, such as 500 and 50. The term "polyol" is meant to include materials having an average of two or more hydroxyl groups per molecule.

Suitable polyols include low molecular weight diols, triols and higher alcohols, low molecular weight amide-containing polyols and higher polymeric polyols such as polyester polyols, polyether polyols, polyurethane polyols, cellulosics, epoxides, polyvinyl alcohols, and hydroxy-containing acrylic interpolymers.

Suitable low molecular weight diols, triols and higher alcohols useful in the present invention include aliphatic polyols, such as alkylene polyols containing from 2 to 18 carbon atoms, non-limiting examples of which include ethylene glycol, 1,4-butanediol, 1,6-hexanediol; cycloaliphatic polyols, such as 1,2-cyclohexanediol and cyclohexane dimethanol. Non-limiting examples of triols and higher alcohols include trimethylol propane, glycerol and pentaerythritol. Also useful are polyols containing ether linkages, such as diethylene glycol and triethylene glycol and oxyalkylated glycerol.

Also useful are higher molecular weight polymeric polyols, such as polyalkylene ether polyols, such as thio ethers, polyester polyols, such as polyhydroxy polyesteramides, and hydroxyl-containing polycaprolactones and hydroxy-containing acrylic interpolymers.

Any suitable polyalkylene ether polyol may be used including those which have the following structural formula:

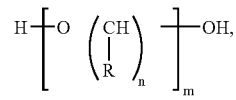

where the substituent R is hydrogen or lower alkyl including mixed substituents, and n is typically from 2 to 6 and m is from 2 to 100 or even higher. Included are poly(oxytetramethylene)glycols, poly(oxyethylene)glycols, polypropylene glycols and the reaction product of ethylene glycol with a mixture of propylene oxide and ethylene oxide.

Also useful are polyether polyols formed from the oxyalkylation of various polyols, for example, glycols such as ethylene glycol, 1,6-hexanediol, Bisphenol A, and the like, or higher polyols, such as trimethylol propane, pentaerythritol and the like. Polyols of higher functionality which can be utilized as indicated can be made, for instance, by oxyalkylation of compounds as sorbitol or sucrose. One commonly utilized oxyalkylation method is the reaction of a polyol with an alkylene oxide, for example, ethylene or propylene oxide, in the presence of an acidic or basic catalyst.

Besides poly(oxyalkylene)glycols, any suitable polyhydric polythioether may be used such as, for example, the condensation product of thioglycol or the reaction product of a polyhydric alcohol with thioglycol or any other suitable glycol.

Polyester polyols can also be used as a polymeric polyol component in the practice of the invention. The polyester polyols can be prepared by the polyesterification of organic polycarboxylic acids or anhydrides thereof with organic polyols. Usually, the polycarboxylic acids and polyols are aliphatic or aromatic dibasic acids and diols.

The diols often employed in making the polyester include alkylene glycols, such as ethylene glycol and butylene glycol, neopentyl glycol and other glycols such as hydrogenated Bisphenol A, cyclohexane diol, cyclohexane dimethanol, caprolactone diol (for example, the reaction product of caprolactone and ethylene glycol), hydroxy-alkylated bisphenols, polyether glycols, for example, poly(oxytetramethylene)glycol and the like. However, other diols of various types and, as indicated, polyols of higher functionality can also be utilized. Such higher polyols can include, for example, trimethylol propane, trimethylol ethane, pentaerythritol, and the like, as well as higher molecular weight polyols such as those produced by oxyalkylating low molecular weight polyols. An example of a high molecular weight polyol is the reaction product of 20 moles of ethylene oxide per mole of trimethylol propane.

The acid component of the polyester often consists primarily of monomeric carboxylic acids or anhydrides having 2 to 18 carbon atoms per molecule. Useful acids include phthalic acid, isophthalic acid, terephthalic acid, tetrahydrophthalic acid, hexahydrophthalic acid, adipic acid, azelaic acid, sebacic acid, maleic acid, glutaric acid, chlorendic acid, tetrachlorophthalic acid and other dicarboxylic acids of varying types. The polyester may include minor amounts of monobasic acid, such as benzoic acid, stearic acid, acetic acid, hydroxy stearic acid and oleic acid. Also, there may be employed higher polycarboxylic acids such as trimellitic acid and tricarballylic acid (where acids are referred to above, it is understood that the anhydrides of those acids which form anhydrides can be used in place of the acid). Also, lower alkyl esters of acids such as dimethyl glutarate can be used. In certain embodiments, the polyester includes an aliphatic dicarboxylic acid as at least part of the acid component.

In addition, polycaprolactone-type polyesters can be used. These products are formed from the reaction of a cyclic lactone such as epsilon-caprolactone with a polyol or a hydroxy acid. Such products are described in U.S. Pat. No. 3,169,949, the portion of this patent relating to the description of polycaprolactone polyols being incorporated herein by reference. The reaction of urea and caprolactone such as described in U.S. Pat. No. 3,832,333 can also be used, the portion relating to the description of this reaction being incorporated herein by reference.

While polyester polyols have been specifically disclosed, it is to be understood that useful products are also obtainable by substituting a polyesteramide polyol, or a mixture of polyesteramide polyols for part or all of the polyester polyol. The polyesteramide polyols are produced by conventional techniques from the above-described acids and diols, and minor proportions of diamines or aminoalcohols. Suitable diamines and aminoalcohols includes hexamethylene diamine, hydrazine, bis(4-aminocyclohexyl)methane, diethylene triamine, ethylene diamine, ethanolamine, phenylene diamine, toluene diamine and poly(amide-amines).

Another suitable class of polymeric polyols is polyurethane polyols, such as polyester-urethane polyols which can be formed by reacting an organic polyisocyanate with a polyester polyol, such as those described above. The organic polyisocyanate can be reacted with a polyol so that the OH/NCO equivalent ratio is greater than 1:1 so that the resultant product contains free hydroxyl groups. The organic polyisocyanate which can be used in preparing the polyurethane polyols can be an aliphatic or aromatic polyisocyanate or a mixture. Diisocyanates are often preferred, although higher polyisocyanates, such as triisocyanates can be used, but they can result in higher viscosities.

Examples of suitable diisocyanates include 4,4'-diphenylmethane diisocyanate, 1,4-tetramethylene diisocyanate, isophorone diisocyanate and 4,4'-methylenebis(cyclohexyl isocyanate). Examples of suitable higher functionality polyisocyanates include polymethylene polyphenol isocyanates.

As indicated, the multifunctional vinyl ethers of certain embodiments of the present invention are the result of a conjugate addition reaction of the nucleophile, in some cases an enolate that is the reaction product of an acetoacetate or malonic ester with, for example, a hydroxy functional compound, with the acrylate group of the vinyl ether group-containing acrylic ester. The Examples herein describe suitable methods and conditions for conducting such reactions and producing such a multifunctional vinyl ether.

As will be appreciated from the foregoing description, certain embodiments of the present invention are directed to multifunctional vinyl ethers comprising a unit represented by the general formula (III), described above, wherein each VE represents the residue of a multi-functional vinyl ether comprising a unit represented by the general formula (I) and may be the same or different, each NU represents the residue of a nucleophile comprising an enolate formed from an acetoacetate or a malonic ester and may be the same or different, R represents the residue of a polyol, and n is an integer having a value of at least 1, such as 1 to 100.

In certain embodiments, the vinyl ethers of the present invention, such as the previously described multifunctional vinyl ethers, have a number average molecular weight of at least 500, such as from 500 to 5000, the molecular weight determined by gel permeation chromatography (GPC) using polystyrene as standard.

The present invention is also directed to compositions, such as "radiation curable" coating compositions or adhesive compositions, comprising a vinyl ether as previously described, such as a previously-described multifunctional vinyl ether. As used herein, the term "radiation curable," when used with reference to a compound, refers to compounds that comprise reactive groups that are capable of being polymerized and/or crosslinked by exposure to actinic radiation, such as an electron beam (EB), UV light, or visible light and, when used with reference to a composition, the term "radiation curable" refers to compositions comprising a radiation curable compound.

In certain embodiments of the compositions of the present invention, the previously described multifunctional vinyl ether is present in an amount of 2 to 98 percent by weight, such as 5 to 95 percent by weight or, in some cases, 10 to 90 percent by weight, based on the total weight of the composition.

In addition to the previously described vinyl ethers, the compositions of the present invention may include other components, such as, for example, cationic and/or free radical photoinitiators. Suitable cationic photoinitiators include onium salts, such as diaryliodonium salts and triarylsulfonium salts that have non-nucleophilic anions, such as hexafluorophosphate, hexafluoroantimonate, tetrafluoroborate and hexafluoroarsenate. Suitable onium salts are described in U.S. Pat. No. 5,639,802, column 8, line 59 to column 10, line 46. Specific examples of suitable onium salts include 4,4'-dimethyldiphenyliodonium tetrafluoroborate, phenyl-4-octyloxyphenyl phenyliodonium hexafluoroantimonate, dodecyldiphenyl iodonium hexafluoroantimonate, [4-[(2-tetradecanol)oxy]phenyl]phenyl iodonium hexafluoroantimonate and mixtures thereof.

In certain embodiments, the radiation curable compositions of the present invention comprise 0.01 up to 15 percent by weight of cationic photoinitiator or, in some embodiments, 0.01 up to 10 percent by weight, or, in yet other embodiments, 0.01 up to 5 percent by weight of cationic photoinitiator, based on the total weight of the composition.

Suitable free radical photoinitiators include, but are not limited to, benzophenones, acetophenone derivatives, such as alpha-hydroxyalkylphenylketones, benzoins such as benzoin alkyl ethers and benzyl ketals, monoacylphosphine oxides, and bisacylphosphine oxides. Free radical initiators are commercially available from, for example, Ciba Specialty Chemicals Corporation in their DURACURE and IRGACURE lines; IRGACURE 184, IRGACURE 651, and DURACURE 1173 are particularly suitable.

In certain embodiments, the radiation curable compositions of the present invention comprise 0.01 up to 15 percent by weight of free radical photoinitiator or, in some embodiments, 0.01 up to 10 percent by weight, or, in yet other embodiments, 0.01 up to 5 percent by weight of free radical photoinitiator based on the total weight of the composition.

In addition, certain embodiments of the compositions of the present invention comprise other radiation curable compounds, aside from the previously described vinyl ethers, including compounds that undergo free radical polymerization and/or compounds that undergo cationic polymerization.

Examples of radiation curable compounds, i.e., monomers, oligomers, and polymers, that undergo free radical polymerization are polymerizable ethylenically unsaturated compounds, mixtures of ethylenically unsaturated compounds and thiols, as well as vinyl ethers aside from the previously described vinyl ethers.

Examples of such polymerizable ethylenically unsaturated monomers which may be present in a composition of the present invention include: acrylic or methacrylic esters, such as methyl(meth)acrylate, ethyl(meth)acrylate, isopropyl(meth)acrylate, n-butyl(meth)acrylate, isobutyl(meth)acrylate, 2-ethylhexyl(meth)acrylate, 2-hydroxyethyl(meth)acrylate, glycidyl(meth)acrylate, ethylene glycol di(meth)acrylate, diethylene glycol di(meth)acrylate, dipropylene glycol di(meth)acrylate, tripropylene glycol di(meth)acrylate, 1,6-hexanediol di(meth)acrylate, tetraethylene glycol di(meth)acrylate, glycerol di(meth)acrylate, glycerol tri(meth)acrylate, glycerol propoxytri(meth)acrylate, 1,3-propylene glycol di(meth)acrylate, 1,2,4-butanetriol tri(meth)acrylate, 1,4-cyclohexanediol di(meth)acrylate, 1,4-benzenediol di(meth)acrylate, pentaerythritol tetra(meth)acrylate, 1,5-pentanediol di(meth)acrylate, trimethylolpropane tri(meth)acrylate, di-trimethylolpropane tetra(meth)acrylate, isobornyl(meth)acrylate and tetrahydrofurfuryl(meth)acrylate; acrylic or methacrylic amides, such as (meth)acrylamide, diacetone(meth)acrylamide, N(beta-hydroxyethyl)(meth)acrylamide, N,N-bis(beta-hydroxyethyl)(meth)acrylamide, methylene bis(meth)acrylamide, 1,6-hexamethylene bis(meth)acrylamide, diethylenetriamine tris(meth)acrylamide, bis(gamma-(meth)acrylamidepropoxy)ethane and beta-(meth)acrylamide ethylacrylate, oxyalkylated versions thereof, as well as mixtures thereof; and vinyl monomers, such as vinyl acetate, n-vinylpyrrolidone, styrene, vinyl toluene and divinyl benzene; as well as mixtures thereof.

In certain embodiments, such polymerizable ethylenically unsaturated monomer(s) are present in the composition in an amount of 5 to 95 percent by weight, such as 50 to 95 percent by weight, or, in some cases, 70 to 95 percent by weight, based on the total weight of the composition.

Examples of polymerizable ethylenically unsaturated oligomers and polymers which may be employed in combination with a vinyl ether of the present invention in a composition of the present invention include ethylenically unsaturated polyesters, including polyester(meth)acrylates, ethylenically unsaturated polyurethanes, ethylenically unsaturated acrylics, and ethylenically unsaturated epoxy resins, as well as mixtures thereof.

Suitable ethylenically unsaturated polyurethanes include those prepared, for example, by reacting polyols such as polyester polyols, polyether polyols, acryl polyols, epoxypolyols or polyurethane polyols with polyisocyanates containing ethylenic unsaturation; by reacting the isocyanate groups of polyurethane resins with unsaturated compounds having active hydrogen atoms such as polymerizable unsaturated carboxylic acids, alcohols, or amines; by reacting hydroxyl groups of polyurethane polyols with unsaturated carboxylic acids or anhydrides thereof; and by reacting carboxyl groups of polyurethane resins with ethylenically unsaturated epoxides. Suitable ethylenically unsaturated acrylics may be prepared, for example, by reacting hydroxyl groups present in side chains of acrylic polymers with unsaturated mono- or polycarboxylic acids (or anhydrides) or with ethylenically unsaturated epoxides; or by reacting carboxyl groups present in side chains of acrylic polymers with ethylenically unsaturated epoxides. Suitable ethylenically unsaturated epoxy resins may be prepared, for example, by reacting polyepoxides with unsaturated carboxylic acids or anhydrides.

Suitable ethylenically unsaturated polyesters include, for example, those prepared by the reaction of unsaturated polycarboxylic acid or anhydride with polyhydric alcohol. Processes for making unsaturated polyesters include batch processes and continuous processes. Often, an unsaturated carboxylic acid having an acid functionality of at least two, more particularly a dicarboxylic acid or its anhydride, is utilized as a starting reactant. Examples of unsaturated dicarboxylic acids and anhydrides include: maleic acid, maleic anhydride, fumaric acid and itaconic acid.

Unsaturated polyesters suitable for use in the present invention may be prepared utilizing a saturated polycarboxylic acid as a portion of the polycarboxylic acid monomers. Thus, from 0 to 90 weight percent of the polycarboxylic acid used in the polyester synthesis may be saturated polycarboxylic acid. Examples of saturated polycarboxylic acids which optionally may be used include phthalic acid, isophthalic acid, terephthalic acid, trimellitic acid, tetrahydrophthalic acid, hexahydrophthalic acid, tetrachlorophthalic acid, adipic acid, azelaic acid, sebacic acid, succinic acid, glutaric acid, malonic acid, pimelic acid, suberic acid, 2,2-dimethylsuccinic acid, 3,3-dimethylglutaric acid, and 2,2-dimethylglutaric acid. Anhydrides of the aforementioned acids, where they exist, and esters of low boiling alcohols such as methanol, also can be utilized.

Examples of polyols suitable for preparing the unsaturated polyester resin include: diethylene glycol, ethylene glycol, propylene glycol, dipropylene glycol, butylene glycol, glycerol, neopentyl glycol, trimethylolpropane, pentaerythritol, sorbitol, 1,6-hexanediol, 1,4-cyclohexanediol, 1,4-cyclohexanedimethanol, and 1,2-bis(hydroxyethyl)cyclohexane. While polyols having a hydroxyl functionality of greater than 2 may be employed in the preparation of the unsaturated polyester resin, it is sometimes preferred that the major portion, if not all, of the unsaturated polyester resin be comprised of unsaturated polyester molecules which are linear, and therefore diols are sometimes preferred.

The unsaturated polyester resins may be prepared by heating the polycarboxylic component and organic polyol component together for about 1 to 10 hours to temperatures of from 165° C. to 250° C., with water formed during the esterification being distilled off using a sparge of an inert gas such as nitrogen. Esterification catalysts for increasing the rate of reaction can also be used. Examples of known catalysts useful for this purpose include para-toluenesulfonic acid, butylstannoic acid, dibutyltin oxide and stannous fluoride. The molecular weight of unsaturated polyester resins suitable for a composition of the invention may vary widely. However, generally the unsaturated polyester resin has a peak molecular weight, as measured by gel permeation chromatography using a polystyrene standard, of from 500 to 50,000, or, in some cases, from 1,000 to 25,000. Some embodiments may include more than one unsaturated polyester.

In certain embodiments of the compositions of the present invention, the multifunctional vinyl ethers described above are cocurable with the ethylenically unsaturated moieties in the backbone of the unsaturated polyester (e.g., provided from the residue of unsaturated carboxylic acid used to make the unsaturated polyester). By "cocurable" is meant that the vinyl ether groups are stable in admixture with the unsaturated polyester resin, but become reactive with the ethylenic unsaturation of the unsaturated polyester upon exposure to ionizing radiation (electron beam radiation) or actinic light (ultraviolet).

In certain embodiments, such compounds that cure by a free radical mechanism, such as the ethylenically unsaturated polyester, are present in an amount of 5 to 95 percent by weight, such as 10 to 90 percent by weight or, in some cases, 25 to 80 percent by weight, based on the total weight of the composition.

Examples of radiation curable compounds, i.e., monomers, oligomers, and polymers, that undergo cationic polymerization include 1,2-, 1,3- and 1,4-cyclic ethers (also designated as 1,2-, 1,3- and 1,4-epoxides), vinyl ethers, cyclic formals, and cyclic organosiloxanes. Examples of cationically polymerizable compounds include diglycidyl ethers of bisphenols, such as 2,2-bis[4-(2,3-epoxypropoxy)phenyl]propane, glycidyl ethers of phenol-formaldehyde novolac, cresyl glycidyl ether, phenyl glycidyl ether, nonylphenyl glycidyl ether, polyglycidyl ethers of castor oil, butyl glycidyl ether, mixed $C_8$-$C_{10}$ or $C_{12}$-$C_{14}$ aliphatic alkyl glycidyl ethers, ethyl hexyl glycidyl ether, cycloaliphatic epoxide monomers, such as the epoxycyclohexanecarboxylates, typified by 3,4-epoxycyclohexylmethyl 3,4-epoxycyclohexanecarboxylate, 3,4-epoxy-2-methylcyclohexylmethyl 3,4-epoxy-2-methylcyclohexanecarboxylate, bis(3,4-epoxy-6-methylcyclohexylmethyl) adipate, 3,4-epoxy-6-methylcyclohexylmethyl 3,4-epoxy-6-methylcyclohexanecarboxylate, vinylcyclohexene dioxide, bis(2,3-epoxycyclopentyl)ether, octadecyl oxide, epichlorohydrin, styrene oxide, glycidol, butyl glycidyl ether, glycidyl acrylate and methacrylate, epoxy modified polypropylene glycol, epoxidized polybutadiene, silicone resins containing epoxy functionality, copolymers of acrylic acid esters of glycidol, such as glycidyl acrylate and glycidyl methacrylate, with one or more copolymerizable vinyl compounds, such as methyl methacrylate, vinyl chloride, and styrene, polymeric epoxides including linear polymers having terminal epoxy groups (e.g. a diglycidyl ether of a polyoxyalkylene glycol), polymers having skeletal oxirane units (e.g. polybutadiene polyepoxide), and polymers having pendent epoxy groups (e.g. a glycidyl methacrylate polymer or copolymer). The backbone may be of any type such that there is an active hydrogen atom which is reactive with an oxirane ring at room temperature. Representative examples of acceptable substituent groups include halogens, ester groups, ether groups, sulfonate ester groups, siloxane groups, nitro groups, and phosphate ester groups. Other cationically-sensitive compounds include vinyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as 1,4-di(ethenoxy)butane, vinyl 4-hydroxy-butyl ether; diethylene glycol divinyl ether, triethylene glycol divinyl ether, bis(4-vinyloxy)butyl)isophthalate, bis [[4-[(vinyloxy)methyl]cyclohexyl]methyl]-terephthalate, bis(4-vinyloxy)butyl)adipate, bis[4-(vinyloxy)butyl]1,6-hexanediylbiscarbamate, tris(4-(vinyloxy)butyl)trimellitate, cyclic formals such as trioxane, 1,3-dioxolane, 2-vinyl-1,3-dioxolane, and 2,-methyl-1,3-dioxolane; and cyclic siloxanes that can contain various groups attached to the silicon atom such as a hydrocarbon radical (alkyl, aryl, alkaryl), an alkenyl hydrocarbon radical (vinyl, allyl or acryloyloxy-alkyl), a halogenated hydrocarbon radical, a carboxy-containing hydrocarbon radical or ester group, a cyanohydrocarbon radical, hydrogen, halogen or a hydroxy group.

In certain embodiments of the compositions of the present invention, such compounds that cure by a cationic mechanism, are present in an amount of 5 to 95 percent by weight, such as 10 to 90 percent by weight or, in some cases, 25 to 80 percent by weight, based on the total weight of the composition.

In certain embodiments, the compositions of the present invention also comprise any of a variety of other additives, such as rheology modifiers, surfactants, UV-light stabilizer, dyes, pigments, sanding additives, antioxidants, solvents, and flatting agents (e.g. wax-coated or non-wax coated silica or other inorganic materials), among other materials.

The radiation curable compositions of the present invention may be applied directly onto the surface of a substrate or over an underlayer by any suitable coating process known to those of ordinary skill in the art, for example, by dip coating, direct roll coating, reverse roll coating, curtain coating, spray coating, brush coating, vacuum coating and combinations thereof. The method and apparatus for applying the composition to the substrate may be determined, at least in part, by the configuration and type of substrate material. Dry film thickness can range from, for example, about 0.1 to 3.0 mils (2.5 to 76.2 microns) per layer, such as 0.2 to 2.0 mils (5.1 to 50.8 microns) per layer or, in some embodiments, 0.2 to 1.0 mil (5.1 to 25.4 microns) per layer.

The compositions of the present invention may be applied to any desired substrates, such as wood, paper, particleboard, chipboard, metals, metals having primers thereon, glass, plastics, and metallized plastics. Once applied, the compositions of the present invention can be cured by radiation. Thus, for example, the compositions of the present invention may be cured by, for example, irradiation with ultraviolet rays, electron beam radiation, as is known to those skilled in the art. In certain embodiments, curing can be completed in less than one minute.

Illustrating the invention are the following examples, which, however, are not to be considered as limiting the invention to their details. Unless otherwise indicated, all parts and percentages in the following examples, as well as throughout the specification, are by weight.

Example 1

A flask was charged with 2-(2'-vinyloxy ethoxy)ethyl acrylate (345.3 g, 1.854 mole, Nippon Shokubai Co., Ltd., VEEA) and potassium carbonate (4.75 g, 0.031 mole). After stirring for 5 minutes at room temperature, diethyl malonate (150.0 g, 0.937 mole) was added over 1 hour. A mild exotherm began 10 minutes after the diethyl malonate addition was complete, and reached a peak temperature of 41° C. three hours after the addition. A $^1$H NMR sample taken 4.5 hours after the addition showed a significant amount of unreacted VEEA. A $^1$H NMR sample taken after the reaction mixture was heated to 75° C. for 4 hours showed no residual VEEA. The crude reaction product was a yellow liquid with a white potassium carbonate precipitate. Ethyl acetate was added and the product was washed with water twice. After drying the organic layer over magnesium sulfate and removing the ethyl acetate under reduced pressure, the isolated product was a clear, colorless liquid. The product had a Gardner-Holdt viscosity of C to D, and the total nonvolatiles were measured at 98.5% (110° C., 60 minutes). Gas chromatographic analysis of the product showed <0.01% diethyl malonate, 0.40% VEEA, and 0.75% ethyl acetate.

Example 2

A flask was charged with VEEA (410.6 g, 2.205 moles) and t-butylacetoacetate (183.5 g, 1.160 moles) and heated to 43° C. with stirring. At 43° C., potassium carbonate (5.82 g, 0.038 moles) was added to the flask. A strong exotherm began within 3 minutes of adding the potassium carbonate. A cool water bath was applied to the flask once the reaction temperature reached 115° C. (11 minutes after adding potassium carbonate), and the temperature dropped to 45° C. over 23 minutes. The temperature was increased to about 70° C. and held for 4.5 hours. A $^1$H NMR sample showed a small amount of unreacted VEEA, so more potassium carbonate (4.85 g, 0.032 mole) was added and the reaction was heated at 70° C. for 7.5 hours. The final $^1$H NMR sample showed no residual VEEA. The crude reaction product was a yellow liquid with a white potassium carbonate precipitate. Silica gel (85 g, Aldrich, grade 60, 70-230 mesh, 60 Å) was stirred with the product for about 4 hours. After heating to 50° C., the mixture was vacuum filtered through a Whatman #4 filter paper. The isolated product was a clear, virtually colorless liquid. The product had a Gardner-Holdt viscosity of I−, and a Gardner color index of 1. Gas chromatographic analysis of the product showed 0.29% VEEA.

Example 3

A flask with a simple distillation setup was charged with 1,6-hexanediol (340.0 g, 2.875 moles) and heated to about 100° C. with stirring. At 100° C., t-butylacetoacetate (864.6 g, 5.465 moles) was added over 30 minutes. Distillate (t-butanol) was collected over about 6 hours at 100° C., and over about 6 more hours at 110° C., and then over 3.5 hours at 110° C. at 50 mmHg. The product had a Gardner-Holdt viscosity of less than A, a hydroxyl number of 28.4 mg KOH/g, an acid value of 0.22 mg KOH/g, and the total nonvolatiles were measured at 99.6% (110° C., 60 minutes). Gas chromatographic analysis of the product showed <0.01% t-butylacetoacetate, <0.01% 1,6-hexanediol, and <0.01% t-butanol.

Example 4

A flask was charged with VEEA (841.2 g, 4.517 moles) and potassium carbonate (10.92 g, 0.072 moles) and heated to about 40° C. with stirring. At 40° C., the reaction product of Example 3 (347.9 g, 2.377 moles) was added over about 80 minutes. The reaction was exothermic, with a peak temperature of 70° C. After the addition was complete, the reaction was held at 70° C. for about 6 hours. The final $^1$H NMR sample showed no residual VEEA. Silica gel (96 g) was stirred with the product for about 15 minutes at 70° C., and the mixture was vacuum filtered through a Whatman #4 filter paper. The isolated product was a clear, virtually colorless liquid. The product had a Gardner-Holdt viscosity of T+, a Gardner color index of 2, and the total nonvolatiles were measured at 98.8% (110° C., 60 minutes). Gas chromatographic analysis of the product showed 0.22% VEEA.

Example 5

A flask equipped with a fractionating distillation setup was charged with molten 1,6-hexanediol (867.0 g, 7.335 mole, preheated to 49° C.) and EMPOL® 1008 (dimer fatty acid, 2133.0 g, Cognis Corporation). A nitrogen sparge was applied and the mixture was heated to 200° C. over about 4 hours with stirring. The acid value was monitored until, after about 10 hours at 200° C., the result was less than 2 mg KOH/g. The product had a Gardner-Holdt viscosity of Z1+, an acid value of 1.63 mg KOH/g, a hydroxyl value of 151.4 mg KOH/g, and the total nonvolatiles were measured at 93.1% (110° C., 60 minutes). Gel permeation chromatography was used to determine a number average molecular weight of 1433 and a weight average molecular weight of 3240.

Example 6

A flask with a simple distillation setup was charged with the polyester product from Example 5 (1500.0 g) and heated to about 100° C. with stirring. At 100° C., t-butylacetoacetate (698.5 g, 3.846 moles) was added over 45 minutes. Distillate (t-butanol) was collected over about 12 hours at 100° C., and over about 4.5 more hours at 110° C., and then over 2 hours at 110° C. at 60 mmHg. The product had a Gardner-Holdt viscosity of W−, a hydroxyl number of 1.8 mg KOH/g, an acid value of 1.27 mg KOH/g, and the total nonvolatiles were measured at 98.8% (110° C., 60 minutes). Gas chromatographic analysis of the product showed 0.29% t-butylacetoacetate, and 0.05% t-butanol. Gel permeation chromatography was used to determine a number average molecular weight of 1341 and a weight average molecular weight of 3242.

Example 7

A flask was charged with VEEA (510.0 g, 2.739 moles) and potassium carbonate (6.84 g, 0.045 moles) and heated to about 40° C. with stirring. At 40° C., the acetoacetate functional polyester product from Example 6 (683.2 g) was added over about 1 hour. After the addition was complete, the reaction was heated to 70° C. (a slight exotherm was observed during heat up, with a peak of 76° C.). After about 17 hours at 70° C., a $^1$H NMR sample still showed residual VEEA. More potassium carbonate (3.42 g, 0.0225 moles) was added and the temperature was increased to about 90° C. After 6 hours at 90° C., a $^1$H NMR sample showed no residual VEEA. Silica gel (96 g) was stirred with the product for about 15 minutes at 70° C., and the mixture was vacuum filtered through a Whatman #4 filter paper. The isolated product was a clear, very slightly yellow liquid. The product had a Gardner-Holdt viscosity of Z2−, a Gardner color index of 3, and the total nonvolatiles were measured at 98.9% (110° C., 60 minutes). Gas chromatographic analysis of the product showed 0.21% VEEA. Gel permeation chromatography was used to determine a number average molecular weight of 1792 and a weight average molecular weight of 3510.

Example 8

Coating compositions were made using the components and the weights in grams shown in Table I. Coatings were prepared by mixing all components with sufficient agitation to uniformly disperse the components.

TABLE I

|  | Coating 1 | Coating 2 | Coating 3 | Coating 4 |
|---|---|---|---|---|
| Modified epoxy diacrylate[1] | 50 | 40 | 40 | 40 |
| Ethoxylated 1,6-hexanediol diacrylate | 50 | 40 | 40 | 40 |
| 1-hydroxy cyclohexyl phenyl ketone | 1 | 1 | 1 | 1 |
| Benzophenone | 1 | 1 | 1 | 1 |
| Tris[4-(vinyloxy)butyl] trimellitate[2] |  | 20 |  |  |
| Product of Example 1 |  |  | 20 |  |
| Product of Example 4 |  |  |  | 20 |

[1]Ebecryl 3500 from Cytec Surface Specialties, Smyrna, GA
[2]Vectomer 5015 product of Morflex, Inc., Greensboro NC, available from Aldrich, Milwaukee, WI Coatings were drawn down at approximately 2 wet mils on steel and on glass plates. Coatings were cured with four medium pressure 80 Watts/cm mercury lamps at 43 ft/min. UVA measured with an EIT Powerpuck radiometer was 1052 millijoules/cm$^2$ and 561 milliwatts/cm$^2$.

Solvent resistance and physical property measurements were obtained for the cured coatings. MEK resistance was determined by rubbing coating surface with solvent soaked cloth. Glass transition temperature, crosslink density, tensile strength and elongation measurements were obtained for cured coatings peeled from glass. DMA results were obtained using a TA Instruments 2980 unit and a heating rate of 3° C./minute. Instron measurements were obtained using a Mini Instron 44 unit with a crosshead speed of 10 millimeters/minute. Results are set forth in Table II.

TABLE II

|  | Coating 1 | Coating 2 | Coating 3 | Coating 4 |
|---|---|---|---|---|
| Resistance to 100 double rubs with methyl ethyl ketone | Some scuffs | Slight scuffs | Some scuffs | No scuff mark |
| Tg (° C.) | 39 | 35 | 30 | 40 |
| Crosslink density (1000 moles/cc) | 4.6 | 3.9 | 4.5 | 6.0 |
| Elongation at Break (%) | 18 | 19 | 24 | 18 |
| Tensile Strength (MPa) | 22 | 19 | 14 | 21 |
| Toughness (MPa) | 3.1 | 2.4 | 1.8 | 2.7 |

Whereas particular embodiments of this invention have been described above for purposes of illustration, it will be evident to those skilled in the art that numerous variations of the details of the present invention may be made without departing from the invention as defined in the appended claims.

We claim:

1. A composition comprising a vinyl ether comprising the conjugate addition reaction product of a nucleophile with the acrylate group of a vinyl ether group-containing acrylic ester represented by the general formula

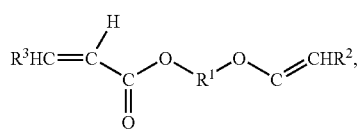

wherein R$^1$ represents an organic residue, and R$^2$ and R$^3$ each represent a hydrogen atom or an organic residue and may be the same or different.

2. The composition of claim 1, wherein the composition is a radiation curable composition.

3. The composition of claim 2, wherein the composition is sprayable.

4. The composition of claim 2, further comprising a compound, different from the vinyl ether of claim 1, which cures via a free radical mechanism and/or a compound that cures via a cationic mechanism.

5. The composition of claim 4, wherein the compound that cures by a free radical mechanism comprises an ethylenically unsaturated compound.

6. The composition of claim 4, wherein the compound that cures by a cationic mechanism comprises an epoxy.

7. A substrate at least partially coated with the composition of claim 2.

8. A radiation curable composition comprising a multi-functional vinyl ether comprising a unit represented by the general formula (II):

wherein each VE represents the residue of a vinyl-ether group containing acrylic ester represented by the general formula

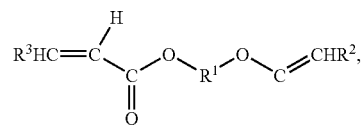

wherein R$^1$ represents an organic residue, and R$^2$ and R$^3$ each represent a hydrogen atom or an organic residue and may be the same or different, and NU represents the residue of a nucleophile.

9. The composition of claim 1, wherein the vinyl ether is a multifunctional vinyl ether.

10. The composition of claim 1, wherein the vinyl ether group-containing acrylic ester comprises 2-(vinyloxyethoxy) ethyl acrylate.

11. The composition of claim 1, wherein the nucleophile comprises an enolate anion formed from a malonic ester or a β-keto ester.

12. The composition of claim 8, wherein NU represents the residue of a compound of the general formula

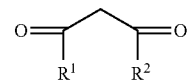

wherein R$^1$ and R$^2$ are organic residues and may be the same or different.

13. The composition of claim 12, wherein R$^1$ is CH$_3$ or OCH$_2$CH$_3$ and/or R$^2$ is OC(CH$_3$)$_3$ or OCH$_2$CH$_3$.

14. The composition of claim 8, further comprising a compound, different from the multi-functional vinyl ether, which cures via a free radical mechanism and/or a compound that cures via a cationic mechanism.

15. The composition of claim 14, wherein the compound that cures by a free radical mechanism comprises an ethylenically unsaturated compound.

16. A substrate at least partially coated with the composition of claim 14.

* * * * *